United States Patent [19]

Trainor

[11] Patent Number: 4,665,909
[45] Date of Patent: May 19, 1987

[54] BANDAGE

[75] Inventor: Fred M. Trainor, Fort Worth, Tex.

[73] Assignee: Avcor Health Care Products, Inc., Fort Worth, Tex.

[21] Appl. No.: 787,155

[22] Filed: Oct. 15, 1985

[51] Int. Cl.⁴ .............................................. A61F 13/00
[52] U.S. Cl. ................................................... 128/155
[58] Field of Search ..................... 128/155, 156, 165

[56] References Cited

U.S. PATENT DOCUMENTS

| | | | |
|---|---|---|---|
| 3,054,400 | 9/1962 | Lizio | 128/163 |
| 3,086,529 | 4/1963 | Munz et al. | 128/327 |
| 3,256,882 | 6/1966 | Huber | 128/165 |
| 3,376,865 | 4/1968 | Gamper | 128/169 |
| 3,480,012 | 11/1969 | Smithers et al. | 128/165 |
| 3,490,450 | 1/1970 | Gardner | 128/166 |
| 3,504,672 | 4/1970 | Moon | 128/169 |
| 3,515,136 | 6/1970 | Baker | 128/166 |
| 3,529,601 | 9/1970 | Kirkland | 128/155 X |
| 3,728,875 | 4/1973 | Hartman | 128/165 |
| 3,787,272 | 1/1974 | Nisbot et al. | 128/156 |
| 3,903,882 | 9/1975 | Augurt | 128/155 |
| 3,993,105 | 11/1976 | Diesner | 139/291 |
| 4,024,003 | 5/1977 | Bühler | 156/148 |
| 4,039,008 | 8/1977 | Diesner | 139/21 |
| 4,484,459 | 11/1984 | Hutson | 66/84 |

FOREIGN PATENT DOCUMENTS

| | | | |
|---|---|---|---|
| 1027018 | 2/1977 | Canada | 139/2 |
| 1015147 | 8/1977 | Canada | 28/5 |
| 1031664 | 5/1978 | Canada | 139/2 |

Primary Examiner—Gregory E. McNeill
Attorney, Agent, or Firm—Kanz, Scherback & Timmons

[57] ABSTRACT

A winding bandage for applying a compressive force to a body part including a knitted fabric strip comprised in part of a hydrophobic primary warp yarn, an elastic secondary warp yarn and a weft yarn. Flexible self closure members are attached to one or both ends of the fabric strip adapted to engage the fabric strip after the bandage has been stretched about the body part so as to secure the bandage thereto.

32 Claims, 13 Drawing Figures

BANDAGE

FIELD OF THE INVENTION

This invention relates generally to bandages and more particularly to elastic winding bandages.

BACKGROUND OF THE INVENTION

Bandages have been devised in the past which comprise an elasticized fabric strip having closure members at one or both ends. The bandage is stretched as it is wrapped about a body part such as a wrist or a knee and then fastened by the closure member on the outermost layer of the bandage. The bandage exerts a compressive force on the body part which is therapeutic for muscle strains, torn ligaments and other ailments. Originally such bandages included metal pins or clamps as a closure device. The metal clamp was mounted on the bandage and presented one or more perpendicular teeth or prongs. To secure the bandage, the prongs of the clamp were inserted into the outer layers of the bandage. However, these clamps were not entirely successful in securing the bandage to the body part and in maintaining the compressive force, particularly as the patient moved. Further, the sharp points of the prongs on the metal clamps are bothersome and potentially injurious to the patient if allowed to penetrate the flesh of the patient. Also, over a period of time the metal clamps tend to tear and damage the bandage material itself.

More recently, bandages have been devised with flexible closure members which are safer and more reliable than the metal clamps. For instance, such closure members have been constructed of Velcro ® material which consists of cooperative hook and loop pile fabric strips. The cooperative strips are attached to opposite sides of the bandage at different points along the length thereof. The bandage is secured to the body part by wrapping it around the body part and bringing the cooperative strips together and is released by pulling the strips apart.

However, although an improvement over metal clamps, such flexible pile closure strips still exhibit undesirable limitations. In particular, adjustment of the diameter of the bandage on the body part and therefore control of the compressive force exerted by the bandage is limited by the relative locations and lengths of the cooperative strips. It is expensive and consequently undesirable to provide either or both of such strips along the entire lengths of both sides of the bandage. Further, such fabric pile closure strips are in and of themselves expensive compared to the cost of the fabric from which the bandage is constructed. Attempts have been made to use only the hook pile portion of the closure member and engage it directly to the bandage itself. These attempts have been unsuccessful as the force required to release such conventional closure members tends to damage and tear the fabric of the bandage. The high level of force required to release the bandage is also undesirable to the patient.

Another problem with conventional winding bandages is the choice of materials used to construct the fabric of the bandage as well as the closure members. Originally cotton or like material was used in conjunction with an elastomeric material to produce a woven fabric with the capability to stretch. Since cotton is not as durable as certain synthetic materials, materials such as polyester have been substituted for cotton. However, these materials were not completely effective when used in close contact with the skin of a patient. Ideally, a bandage should be constructed to draw fluids and secretions, such as blood, sweat and other body liquids, from the skin of the patient and conduct them to the exterior surface of the bandage where they will evaporate or collect for disposal when the bandage is removed. Conventional bandage materials such as cotton and polyester do not possess this property and therefore do not satisfactorily solve all of the above indicated problems.

SUMMARY OF THE INVENTION

This invention provides a winding bandage. The fabric of the bandage is preferably knitted using primary warp yarns formed from a hydrophobic polymer such as polypropylene. Cotton or like material is used as a weft or filling yarn. Elastic threads are also used as secondary warp strands to enable the bandage to stretch and apply a compressive force to a body part. Flexible pile fabric strips having inclined hooks with semi-spherically shaped head portions are attached to the front and back sides of the fabric at opposite ends of the strip to serve as closure members. Alternatively, the head portions may be spherically shaped and stand either upright or be inclined. The closure members releasably grip the bandage fabric anywhere along its length without requiring a cooperative pile loop fabric anywhere along its length and without damaging the bandage fabric when being disengaged therefrom. In an alternate embodiment of the invention, the bandage fabric is constructed by extruding a continuous sheet of polypropylene or like hydrophobic material in a hexagonal shaped cell pattern and floating the elastic secondary warp strands in the pattern.

Therefore, it is a principal feature and advantage of this invention to provide an improved elastic winding bandage having flexible closure members which releasably grip the fabric of the bandage to secure the bandage to a body part.

It is another feature and advantage of this invention to provide an improved elastic winding bandage which draws fluids away from the skin.

It is yet another feature and advantage of this invention to provide an improved elastic winding bandage which reduces the force required to release and remove the bandage from a patient.

It is another advantage of this invention to provide an improved winding bandage which is self adhering.

BRIEF DESCRIPTION OF THE DRAWINGS

So that the manner in which the above recited features and advantages of the invention, as well as others which will become apparent to those skilled in the art, are obtained and can be understood in detail, a more particular description of the invention briefly summarized above may be had by reference to the embodiments thereof which are illustrated in the accompanying drawings, which drawings form a part of the specification and in which like numerals depict like parts in the several views. It is noted, however, that the appended drawings illustrate only a preferred embodiment of the invention and are therefore not to be considered limiting of its scope, for the invention may admit to other equally effective embodiments.

DETAILED DESCRIPTION OF THE INVENTION

Figure 1:
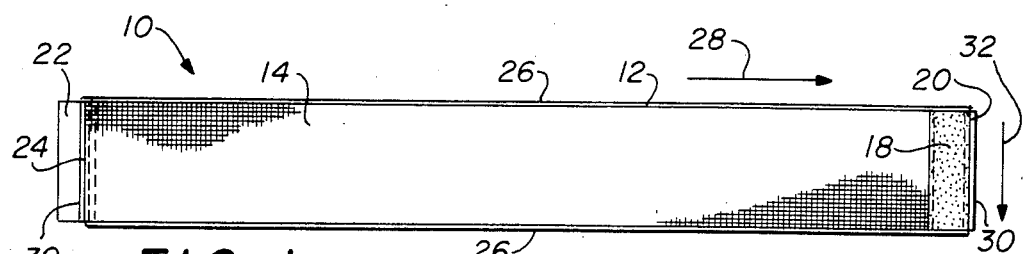
FIG. 1 is a top view of the front side of a bandage according to this invention.
Figure 2:
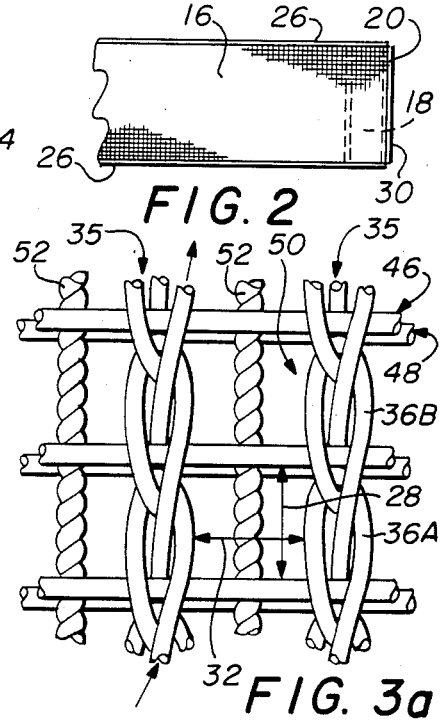
FIG. 2 is a top view of a portion of the back side of the bandage of FIG. 1.

Referring now to FIGS. 1 and 2, there is shown at 10 an elastic winding bandage according to this invention and including fabric strip 12. The fabric strip defines front side 14 shown in FIG. 1 and back side 16 partially shown in FIG. 2. For the purposes of this invention, the front side of the bandage is that side which is intended to be displayed outwardly when the bandage is applied to a body part. The back side is the opposite side of the bandage and is intended to face inwardly and is not normally displayed when in use. First closure member 18 is mounted, such as by sewing or ultrasonic bonding, adjacent first end 20 of the fabric strip on the front side and extends the full width of the fabric strip but only a relatively short portion of its length. As shown particularly in FIG. 2, second closure member 22 is mounted, also such as by sewing or ultrasonic bonding, on the fabric strip adjacent second end 24 of the strip and on the back side thereof. A portion of the second closure member extends beyond the end of the fabric strip.

Selvage strips 26 are incorporated into the fabric in a manner known to the art along both edges parallel with longitudinal direction 28 as the fabric is being knitted to protect the fabric from unraveling and to prevent it from "rolling" during use. That is, the selvage strips act to stop the material from being distorted or wrinkled. The selvage strips are formed from a single strand, multi-filament yarn and may be constructed of material such as nylon having a high degree of strength and wear resistance. Serging strips 30 are incorporated at each end of the fabric strip parallel with transverse direction 32 during the knitting process in a manner known to the art and also act to prevent the fabric from rolling or unraveling during use. A polyester single strand, multi-filament yarn may be employed for the serging strips. In addition, the serging strips may be color coded to indicate, for instance, the width of a particular bandage as compared to other bandage widths.

Figure 3:
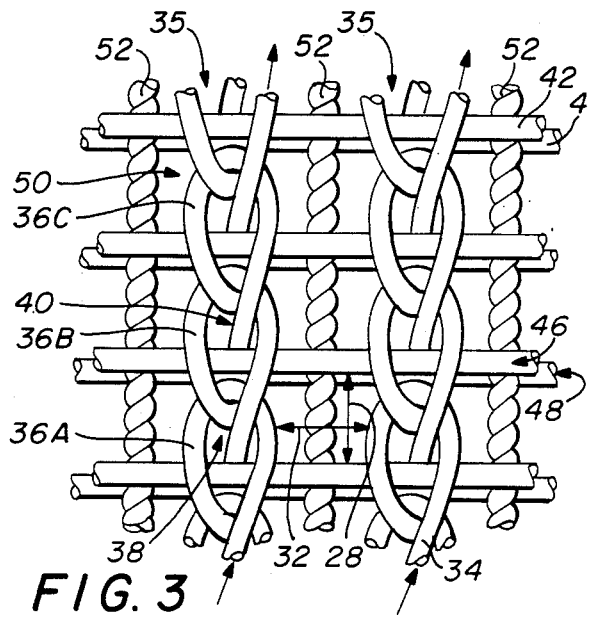
FIG. 3 is a magnified view of a portion of the front side of the bandage of FIG. 1 in a relaxed state.
Figure 4:
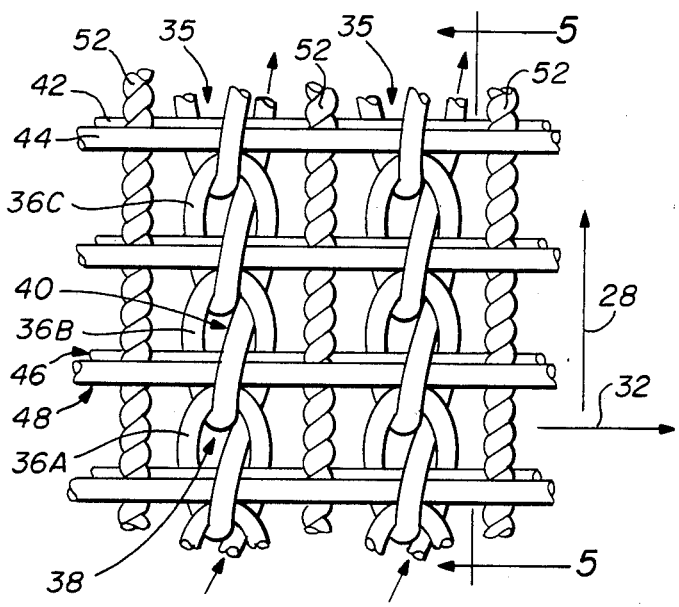
FIG. 4 is a magnified view of a portion of the back side of the bandage of FIG. 2 in a relaxed state.
Figure 5:
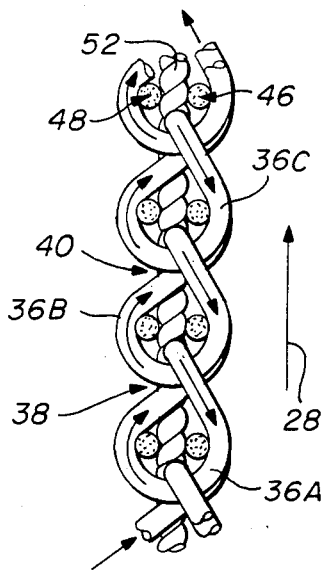
FIG. 5 is a cross-sectional view of the bandage of FIG. 4 along plane 5—5.

FIGS. 3 and 4 show a magnified portion of the front and back sides, respectively, of the fabric strip in a relaxed or unstretched state. Fabric strip 12 may be constructed in many different patterns known to the art. However, in the preferred embodiment of the invention, the fabric strip includes a plurality of knitted warp yarns 34 forming individual, unconnected wales or columns 35 extended the full length of the fabric strip parallel with longitudinal direction 28. The primary warp yarn in each wale forms a series of interconnected loops such as those labeled 36A, 36B and 36C in FIGS. 3 and 4. Loop 36B extends first in longitudinal direction 28 then back in a reverse direction to extend through and engage adjacent loop 36A at 38. Loop 36A then continues toward back side 16 of the fabric and then toward the front side. The primary yarn then passes back through loop 36B at 40 and continues in direction 28 to form loop 36C. A portion of loop 36C extends back to pass through loop 36B and so on in a similar pattern. Front and back strands of weft or filling yarn 42 and 44, respectively, are interwoven or floated with the knitted wales of the warp yarns in transverse direction 32 between each side edge of the fabric in a manner known to the art defining a plurality of aligned front and back courses 46 and 48, respectively. Each "pick" or course of front and back weft yarn passes through and engages each loop of warp yarn aligned with that course of fabric as shown in FIG. 5.

Figure 3A:
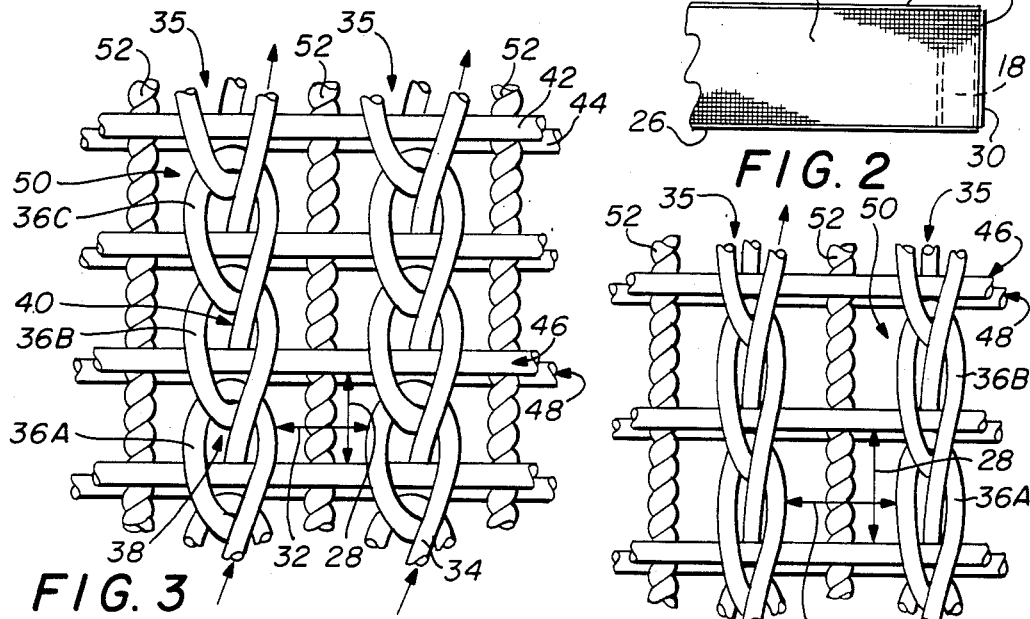
FIG. 3A is a magnified view of the portion of the bandage in FIG. 3 in a stretched state.

The primary warp yarn and the front and back weft yarns form a relatively open fabric with large, generally square openings or windows 50 defined thereby at regular intervals. A plurality of secondary warp strands 52 are longitudinally interlayed or floated between the front and back courses of the weft yarn and between and parallel with each of the wales of the primary warp yarn. The front courses of weft yarn are thus spaced from the back courses of weft yarn by the thickness of the secondary warp strands as illustrated in FIG. 5. The secondary warp yarn exhibits elastic properties and may be constructed of rubber or synthetic strands. The secondary warp strands enable the fabric to be stretched and to exert a compressive force when secured on a body part. As the fabric is being stretched, the loops of the primary warp yarn will contract from side to side in transverse direction 32 and lenthen in longitudinal direction 28 as shown in FIG. 3A. At the same time, the weft yarns will be carried by the loops in the warp yarn and become spread further apart in longitudinal direction 28. Consequently, both the longitudinal and the transverse dimensions of the windows will be increased by approximately the same factors. Therefore, the windows remain substantially square, even when the bandage is fully stretched. The primary warp yarn and the front and back weft yarns, both being essentially inelastic, inherently restrict the elongation of the bandage as the loops become taut and completely stretched out. This provides a restriction on the compressive force exerted by the bandage within safe, predetermined limits.

Primary warp yarn 34 is preferably a single stranded, multi-filament yarn constructed of material having well developed hydrophobic properties. In other words, the material is extremely resistant to absorption of water or moisture. In the preferred embodiment of the invention, polypropylene is used as the primary warp yarn material. Polypropylene has a specific gravity of 0.91 and is therefore relatively lightweight as opposed to other conventional winding bandage materials such as polyester having a specific gravity of between 1.22 to 1.38. Further, polypropylene possesses high strength and has superior hydrophobic properties (see Understanding Textiles, Phyllis G. Tortora, Macmillan Publishing Co., Inc. 1978, pps. 135-137). Cotton may be employed for the front and back weft yarns. However, preferably the front and back weft yarns are constructed of an equal blend of cotton and polyester formed into separate multi-filament, single stranded yarns. The weft yarns also provide the fabric with a texture on the back side of the bandage which is more comfortable in contact with skin when the bandage is in use.

Figure 6:
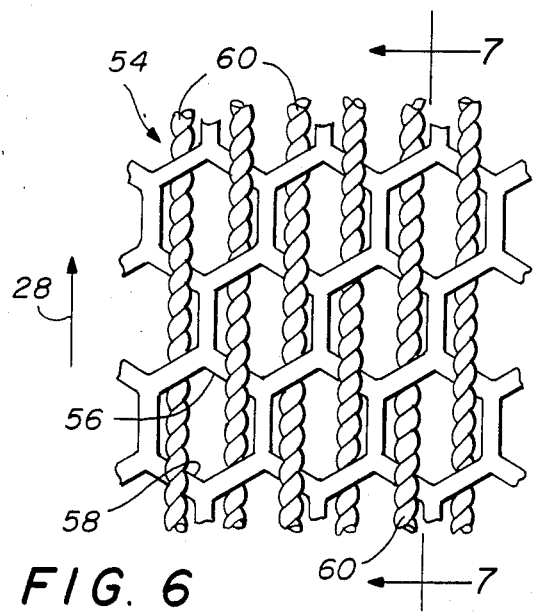
FIG. 6 is a magnified view of an alternate embodiment of the bandage of this invention in a relaxed state.
Figure 7:
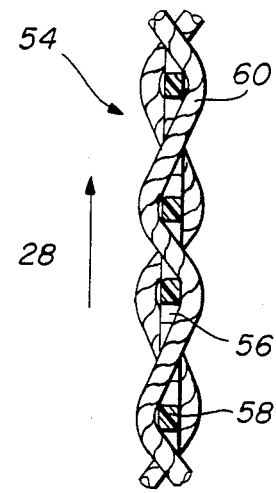
FIG. 7 is a cross-sectional view along plane 7—7 of the bandage of FIG. 6.

Turning now to FIGS. 6 and 7, an alternate embodiment of the fabric is illustrated in which a continuous sheet 54 of extruded polypropylene is formed. The polypropylene sheet includes a continuous matrix of six-sided cells 56 defining windows 58 of approximately equal area to the windows shown in FIGS. 3 and 4. Preferably, the six-sided cells are uniformly hexagonal in shape, although the relative lengths of the walls of the cells may be varied if desired. Further, cells having less or more than six walls, such as square or octagonal cells, may be employed if desired. The hexagonal cells incorporate the function of both the primary warp yarns and the front and back weft yarns in defining the fabric as in the previous embodiment. Elastic secondary warp strands 60 are floated within the matrix of polypropylene cells and act as previously described to apply a compressive force when the bandage is applied to a body part. The elongation of the bandage in a longitudinal direction is limited by the size and shape of the cells in the matrix. That is, the cells of the sheet will become elongated in longitudinal direction 28 and narrower in transverse direction 32 as the bandage is being stretched. However, in all other respects the bandage of this embodiment functions as in the first embodiment and may be attached to similar closure members.

Figure 8:
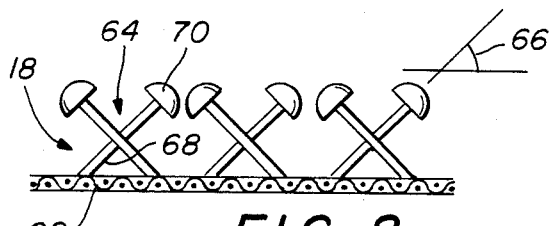
FIG. 8 is a magnified view in cross-section of the closure member of the bandage of FIG. 1.
Figure 9:
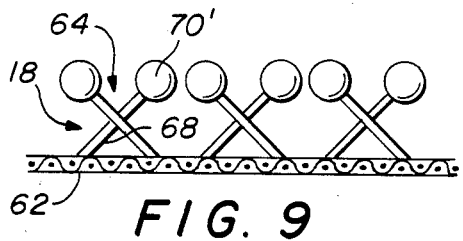
FIG. 9 is a magnified view in cross-section of an alternative closure member.

A detailed cross-sectional view of a portion of first flexible pile closure member 18 is shown in FIG. 8 including base sheet or closure strip 62 and plurality of hooks 64. The base sheet comprises a woven sheet of nylon, whereas the inclined hooks are floated within the nylon warp and weft strands. Preferably, the hooks are constructed from polypropylene. The hooks project outwardly from the base sheet at angle 66 which is preferably 45°. The hooks each include elongated, flexible stalk portion 68 projecting outwardly of the base sheet terminating in head portion 70. In FIG. 8 the head portion of the hook is mushroom-shaped or semi-spherical. FIG. 9 shows an alternate design for the hook in which head portions 70' are spherical or lollipop-shaped. Other shapes or configurations for the head portions or the hooks may also be devised.

Figure 10:
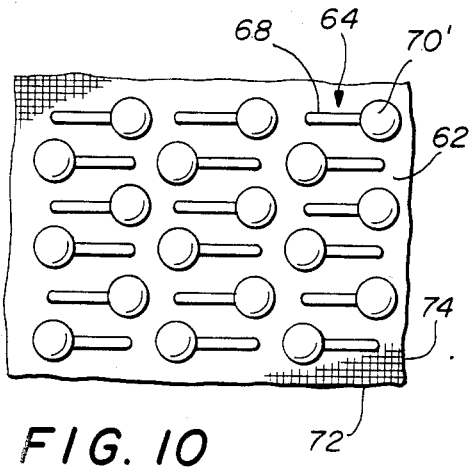
FIG. 10 is a top view of the portion of the closure member of FIG. 9.

FIG. 10 shows one possible arrangement of the hooks on the base sheet aligned in columns 72 and rows 74 with alternating hooks in each column inclined in opposite directions but with all hooks in the same row inclined in the same direction. As shown in either FIG. 8 or FIG. 9, the stalk portions of adjacent hooks in each column are connected to the base sheet at spaced points so that the stalk portions cross over and support their respective head portions at approximately the same height above the base sheet. Of course, other patterns for the hooks may be devised or the hooks may be placed randomly thereon if desired. Although not shown in detail, second closure member 22 is constructed in a similar fashion and functions as herein described with respect to the first closure member. Referring again to FIGS. 1 and 2, first closure member 18 is attached to the fabric strip with the hooks presented toward the front side of the bandage. Conversely, second closure member 22 is attached to the fabric strip with the hooks presented to the back side of the bandage and are therefore not visible in FIG. 1.

In conventional flexible hook closure members, the hooks have mushroom-shaped heads and stand upright to maximize the gripping force with which the closure member engages the cooperative loop closure strip. U.S. Pat. No. 4,024,003 issued to Buhler describes a method for forming upright hook closure members having the mushroom-shaped heads. As previously discussed, such conventional designs are designed for use with cooperative loop pile fabric strips and are too strong for use directly with the fabric of a bandage. However, the inclination of the hook closure members of the present invention in combination with the relatively large and accessible windows in the fabric cooperate to control and limit the gripping force of the closure member to a level which will not damage the fabric of the bandage even after repeated uses.

When the closure strip of this invention is pressed on the fabric strip, a plurality of the hooks will enter each of the windows. Those hooks adjacent the primary warp yarns and the weft yarns defining the windows will securely engage those yarns by the head portion to secure the close member to the fabric. If the warp and weft yarns are single strand, multifilament yarns, the hooks penetrate the yarn strands and the head portions of the hooks catch on the individual filaments or fibers forming the yarn. When the closure member is being pulled from the fabric strip of the bandage, the direction of the pulling force is substantially perpendicular to the fabric. If the hooks are upright, as in conventional closure members, the mushroom shaped heads of the hooks will present a flat, bottom surface parallel with the fabric. The hooks must be deflected from the upright position in order to allow the filaments of the strands to slip off the head portion and release the closure member from the fabric. The level of force required to accomplish this places a stress on the yarn filaments which tends to damage or break them. The inclined hooks of the present invention reduce the level of force required to release the closure member, since it is not necessary to deflect them from an upright position, yet securely adhere to the fabric strip during use.

In the embodiment of the heads shown in FIG. 9, the spherical shape of the heads further reduces the force necessary to release the closure member from the fabric than the embodiment shown in FIG. 8. In this embodiment of the invention, the bottom flat surface of the mushroom-shaped heads are replaced by a spherical surface. Since the lollipop-shaped head further reduces the force required to release the closure member from the fabric strip, it is possible with this embodiment to increase the angle of inclination of the hooks up to and including standing upright as in conventional hook manners without increasing the release force to a level which will damage the fabric strip. In either embodiment, the strands of the fabric are placed under less stress than in conventional bandages, even after repeated uses, and the level of force may be controlled not only by the shape of the head portions but also by adjusting the angle of the head portions with respect to the base sheet of the closure members or by the density of hooks on the base sheet.

As an example, a bandage according to this invention which is twenty-four inches long and three inches wide may be constructed with forty-one wales of primary warp yarn along with two edge wales of selvage. The warp primary yarn used in this example is constructed of sixty-eight individual polypropylene filaments or fibers, each measuring one hundred fifty denier. The selvage yarn is constructed of thirty-four individual nylon filaments, each measuring seventy denier. The front and back weft yarns of the example are each constructed of a polyester/cotton blend which includes thirty individual fibers of material. The front and back weft yarns are interwoven into the fabric at thirty-two picks per inch to provide the necessary spacing with the primary warp yarn wales to form the windows. The secondary warp yarn is constructed of sixty gauge rubber and, since the secondary yarn is interposed between each of the primary wales and the selvage wales, the example bandage includes forty-two total wales of secondary warp yarn. As measured in terms of percent elongation from the unstretched length of the fabric strip, an elongation factor of between 140% and 200% has been found to be advantageous and, in particular, an elongation factor of 170%±5% provides the best characteristics for a bandage constructed according to this invention. As applied to the specific example cited herein, the three inch wide bandage including a closure member as hereinabove described would require a minimum peel force of 0.30 PIW (pounds of force per inch of bandage width) to disengage the closure member from the front side of the fabric with an average peel force of 0.62 PIW. Such a closure member would also require a minimum shear force of 1.30 p.s.i. and an average shear force of 1.80 p.s.i. to remove it from the bandage. The closure member would not as readily engage the back side of the bandage since the loops of the primary warp yarns are not as accessible as on the front side and therefore the comparable peel and shear force levels would be somewhat lower. In comparison, conventional flexible pile fabric closure members, such as the Velcro ® hook and loop fastener previously discussed, require a higher shear force (approximately 3.7-11.2 p.s.i.) and require a higher peel force (approximately 0.35-1.00 PIW) to disengage the fastener members from each other.

Figure 11A:
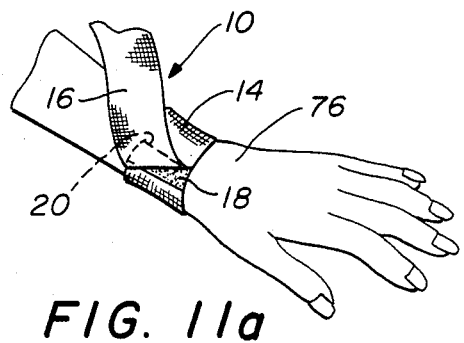
FIG. 11A is a perspective view of the bandage of this invention partially applied to a body part.
Figure 11B:
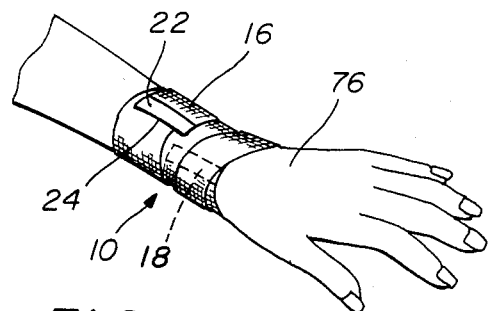
FIG. 11B is a perspective view of the bandage of FIG. 11A fully applied to a body part.

In operation, the bandage of this invention is easily applied to any three dimensional form as shown in FIGS. 11A and 11B. In FIG. 11A, body part 76, which is shown as a wrist is presented for treatment by bandage 10. First end 20 of the bandage is placed directly on the wrist with back side 16 in contact with the skin of the patient and front side 14 and first closure member 18 displayed outwardly. As a result of the higher proportion of primary warp strands visible on the front side of the bandage, compared to the back side, the front side has a much more shiny appearance to the eye and thus may easily be differentiated from the back side. The bandage is then wrapped about the wrist while simultaneously being stretched. The level of compressive force applied is determined by the amount of stretch introduced into the bandage fabric. As the first layer of the bandage is brought around the back side of the fabric strip is pressed into the first closure member to secure the first layer of the bandage on the wrist. As previously described, the closure members are not as effective in gripping the back side of the fabric strip as compared to the front side due to the higher proportion of the primary warp yarn on the front side. However, the first closure member grips the back side of the bandage securely enough to maintain the position of the bandage on the wrist while the remainder of the bandage is being stretched and wrapped about the wrist.

As shown in FIG. 11B the bandage is fully wrapped and second closure member 22 is pressed into front side 14 of the bandage on the outermost layer thereof. The bandage is now secure and will apply a continuous compressive force to the body part until removed by releasing the second closure member and unwrapping the bandage from the wrist and removing the first closure member. If it is desired to reduce or to increase the compressive force of the bandage, it is merely necessary to release the second closure member from the outermost layer of the fabric strip and relax or increase the stretch of the bandage and then reapply the second closure member. Since the closure member engages the material of the bandage, the compressive force is infinitely adjustable from totally relaxed to the maximum elongation of the bandage.

One of the inherent advantages of the bandage herein described is that the fabric strip acts to draw fluids and secretions from the skin to the outer layers of the bandage. The hydrophobic nature of polypropylene prevents substantial amounts of the fluids from being absorbed by the material of the bandage as is the case with conventional bandages constructed from cotton or polyester which tend to hold the fluids adjacent the skin until the bandage is removed. Further, the knit pattern shown in FIGS. 3, 3A, 4 and 5 is particularly adapted for drawing fluids and secretions away from the skin of the wearer and thus enhances the hydrophobic properties of the bandage. The present invention thus increases the safety and comfort of the wearer of the bandage.

Although the invention has been disclosed above with regard to particular and preferred embodiments, these are advanced for illustrative purposes only and are not intended to limit the scope of this invention. Specifically, the fabric strip of this invention may be knitted by any pattern found advantageous or may even be woven. For instance, other patterns may provide a fabric with identical front and back sides so that the closure members engage either side with equal effectiveness. Further, materials other than polypropylene may be employed having hydrophobic properties with equal effectiveness. The weft yarns and the secondary warp fibers may also be constructed from hydrophobic material to enhance the ability of the bandage to draw fluids away from the skin of the wearer. Finally, the first closure member may be omitted, if desired, and the bandage secured to the body part solely by the second closure member. These variations remain within the invention as claimed below.

What is claimed is:

1. A winding bandage for applying a compressive force to a body part comprising:
    (a) a fabric strip defining a front side and a back side and comprising
        plurality of wales of knitted primary warp yarn constructed of hydrophobic material adapted to draw fluids away from the body part,
        a plurality of courses of weft yarns floated in said wales of primary warp yarn thereby defining a plurality of windows between said primary warp yarns and said weft yarns, and
        a plurality of elastic secondary warp yarns floated in said courses of weft yarns enabling the bandage to be elongated while being wrapped about the body part so as to apply a compressive force thereto; and
    (b) at least one flexible closure member attached to one end of said fabric strip and adapted to releasably engage said fabric strip so as to secure the bandage to the body part.

2. The bandage of claim 1 wherein the bandage further includes selvage strips incorporated into the fabric strip along at least a portion of the longitudinal edges thereof.

3. The bandage of claim 1 wherein the bandage further includes serging strips incorporated into at lest a portion of one end edge thereof.

4. The bandage of claim 1 wherein the elongation factor for the bandage is between 140% and 200%.

5. The bandage of claim 1 wherein the elongation factor for the bandage is approximately 170%.

6. The bandage of claim 1 wherein the bandage further includes a first flexible closure member attached to a first end of said fabric strip and directed toward said front side of said fabric strip and a second flexible closure member attached to a second end of said fabric strip and directed toward said back side of said fabric strip.

7. The bandage of claim 1 wherein said flexible closure member comprises a flexible strip attached to said fabric strip and including a plurality of inclined hooks supported in said closure strip, each of said hooks having a stalk portion projecting from said closure strip and terminating in a head portion adapted for insertion into said windows of said fabric strip and engagement with said primary warp yarns and said weft yarns so as to secure said closure member to said fabric strip.

8. The bandage of claim 7 wherein said hooks of said closure members are inclined at an angle of approximately 45°.

9. The bandage of claim 7 wherein said head portions of said inclined hooks are semi-spherically shaped.

10. The bandage of claim 7 wherein said head portions of said inclined hooks are spherically shaped.

11. The bandage of claim 1 wherein said primary warp yarns are constructed of polypropylene.

12. The bandage of claim 1 wherein said flexible closure member comprises a flexible strip attached to said fabric strip and including a plurality of hooks supported in said closure strip, each of said hooks having a stock portion projecting from said closure strip and terminating in a spherically shaped head portion adapted for insertion into said windows of said fabric strip in engagement with said primary warp yarns and said weft yarns so as to secure said closure member to said fabric strip.

13. The bandage of claim 1 wherein said primary warp yarns are single strand, multi-filament yarn constructed of polypropylene.

14. A winding bandage for applying compressive force to a body part comprising:
(a) a fabric strip defining a front side and a back side and comprising
a plurality of knitted wales of single strand, multi-filament primary warp yarn constructed of hydrophobic material adapted to draw fluids away from the body part,
a plurality of aligned front and back courses of single strand, multi-filament weft yarns floated in said wales of primary warp yarn thereby defining a plurality of windows between said primary warp yarns and said weft yarns, and
a plurality of elastic secondary warp yarns floated between said front and back courses of weft yarns enabling the bandage to be elongated while being wrapped about the body part as as to apply a compressive force thereto; and
(b) at least one flexible closure member attached to one end of said fabric strip and adapted to releasably engage said fabric strip so as to secure the bandage to the body part.

15. The bandage of claim 14 wherein the bandage further includes a first flexible closure member attached to a first end of said fabric strip and directed toward said front side of said fabric strip and a second flexible closure member attached to said fabric strip and directed toward said back side of said fabric strip.

16. The bandage of claim 14 wherein said flexible closure member comprises a flexible strip attached to said fabric strip and including a plurality of inclined hooks supported in said closure strip, each of said hooks having a stalk portion projecting from said closure strip and terminating in a head portion adapted for insertion into said windows of said fabric strip and engagement with said primary warp yarns and said front and back weft yarns so as to secure said closure member to said fabric strip.

17. The bandage of claim 16 wherein said hooks of said closure member are inclined at an angle of approximately 45°.

18. The bandage of claim 16 wherein said head portions of said inclined hooks are semi-spherically shaped.

19. The bandage of claim 16 wherein said head portions of said inclined hooks are spherically shaped.

20. The bandage of claim 14 wherein said flexible closure member comprises a flexible strip attached to said fabric strip and including a plurality of hooks supported in said closure strip, each of said hooks having a stock portion projecting from said closure strip and terminating in a spherically shaped head portion adapted for insertion into said windows of said fabric strip in engagement with said primary warp yarns and said weft yarns so as to secure said closure member to said fabric strip.

21. The bandage of claim 14 wherein said hydrophobic primary warp yarns are constructed of polypropylene.

22. A flexible closure member for use with a winding bandage having an elastic fabric strip comprising
a flexible closure strip adapted for attachment to the fabric strip of the bandage and including a plurality of spaced hooks supported in said closure strip, each of said hooks having a stalk portion projecting from said closure strip and terminating in a head portion adapted for insertion into the fabric strip and engagement therewith so as to secure said closure member to said fabric strip.

23. The flexible closure member of claim 22 wherein said inclined hooks are formed in aligned rows on said closure strip.

24. The flexible closure member of claim 23 wherein adjacent rows in each of said columns of said hooks are inclined in opposite directions.

25. The flexible closure member of claim 22 wherein said hooks of said closure members are inclined at an angle of approximately 45° with respect to said closure strip.

26. The flexible closure member of claim 22 wherein said hooks are inclined with respect to said closure strip and wherein said head portions of said inclined hooks are semi-spherically shaped.

27. The flexible closure member of claim 22 wherein said head portions of hooks are spherically shaped.

28. A fabric strip for use in a winding bandage for applying compressive force to a body part, the fabric strip adapted for attachment to one or more closure members, comprising:
(a) a plurality of wales of a knitted primary warp yarn constructed of a hydrophobic material adapted to draw fluids away from the body part;
(b) a plurality of courses of weft yarn floated in said wales of primary warp yarn, thereby defining a plurality of windows between said primary warp yarns and said weft yarns; and
(c) a plurality of elastic secondary warp yarns floated in said courses of weft yarn enabling the fabric strip to be elongated while being wrapped about the body part so as to apply a compressive force thereto.

29. A fabric strip defining a front side and back side adapted for attachment to one or more closure members for use in a winding bandage for applying compressive force to a body part comprising:
(a) a plurality of knitted wales of a single strand multi-filament primary warp yarn constructed of hydrophobic material adapted to draw fluids away from the body part;
(b) a plurality of aligned front and back courses of a single strand multi-filament weft yarns floated in said wales of primary warp yarn thereby defining a plurality of windows between said primary warp yarns and said front and said back weft yarns; and
(c) a plurality of elastic secondary warp yarns floated between said front and said back courses of weft yarns enabling the bandage to be elongated while being wrapped about the body part so as to apply compressive force thereto.

30. The fabric strip of claims 28 or 29 wherein the elongation factor for the fabric strip is between 140% and 200%.

31. The bandage of claims 28 or 29 wherein the elongation factor for the fabric strip is approximately 170%.

32. The fabric strip of claim 28 wherein said hydrophobic primary warp yarns are constructed of polypropylene.

* * * * *

UNITED STATES PATENT AND TRADEMARK OFFICE
CERTIFICATE OF CORRECTION

PATENT NO. : 4,665,909
DATED : May 19, 1987
INVENTOR(S) : Fred M. Trainor

It is certified that error appears in the above-identified patent and that said Letters Patent is hereby corrected as shown below:

In Column 4, line 41   change "lenthen" to ---lengthen---

In Column 9, line 8,   change "lest" to ---least---

In Column 10, line 1,  change "as as" to ---so as---

Signed and Sealed this

Twenty-ninth Day of September, 1987

Attest:

DONALD J. QUIGG

*Attesting Officer*    *Commissioner of Patents and Trademarks*